US009486351B2

(12) United States Patent
Pegg

(10) Patent No.: US 9,486,351 B2
(45) Date of Patent: Nov. 8, 2016

(54) ULNAR SIDED WRIST SUPPORT BRACE

(71) Applicant: Kristy Pegg, Massilon, OH (US)

(72) Inventor: Kristy Pegg, Massilon, OH (US)

( * ) Notice: Subject to any disclaimer, the term of this patent is extended or adjusted under 35 U.S.C. 154(b) by 443 days.

(21) Appl. No.: 14/055,167

(22) Filed: Oct. 16, 2013

(65) Prior Publication Data
US 2015/0105709 A1    Apr. 16, 2015

(51) Int. Cl.
A61F 5/01     (2006.01)
A61F 5/058    (2006.01)
A61F 7/00     (2006.01)

(52) U.S. Cl.
CPC ............ A61F 5/013 (2013.01); A61F 5/05866 (2013.01); A61F 2007/0035 (2013.01)

(58) Field of Classification Search
CPC ...................................................... A61F 5/013
USPC ............ 128/878, 879; 5/600, 621, 623, 646, 5/630; 2/159, 161.1, 161.2, 161.4, 162, 2/170, 908, 910, 912, 917, 455, 16
See application file for complete search history.

(56) References Cited

U.S. PATENT DOCUMENTS

| | | | | |
|---|---|---|---|---|
| 3,512,776 A | * | 5/1970 | Thomas, Sr. | ........ A41D 13/088 2/161.7 |
| 3,704,994 A | * | 12/1972 | Krzewinski | .......... A41D 13/088 2/170 |
| 4,584,993 A | * | 4/1986 | Nelson | ................... A61F 5/0118 602/21 |
| 5,513,657 A | * | 5/1996 | Nelson | .................. A61F 5/0118 128/879 |
| 5,730,711 A | | 3/1998 | Kendall et al. | |
| 5,759,166 A | * | 6/1998 | Nelson | ................... A61F 5/0118 602/21 |
| 5,928,172 A | | 7/1999 | Garlord | |
| 2004/0019306 A1 | * | 1/2004 | Brewer | .................... A61F 5/013 602/21 |
| 2005/0267391 A1 | | 12/2005 | Garelick | |
| 2008/0228120 A1 | | 9/2008 | Gill | |
| 2013/0226056 A1 | * | 8/2013 | Palo, Jr. | .............. A61F 5/05866 602/21 |
| 2013/0226057 A1 | * | 8/2013 | Palo, Jr. | ................. A61F 5/0118 602/22 |

* cited by examiner

*Primary Examiner* — Tarla Patel
(74) *Attorney, Agent, or Firm* — Lynn & Lynn; John H Lynn

(57) ABSTRACT

A wrist brace includes a base panel having inner and outer surfaces. The base panel has a thumbhole and a strap slit therein. A wrist strap is connected to the inner surface of the base panel and formed to wrap around a patient's wrist directly over the ulnar styloid to provide volar compression. An oblique strap having is connected to the outer surface of the base panel and arranged to wrap from the patient's volar radial wrist over the patient's ulnar carpus at an oblique angle on the base panel with the second oblique strap end attaching to the outer surface of the base panel dorsally near the distal to mid-shaft area of the patient's second metacarpal.

3 Claims, 4 Drawing Sheets

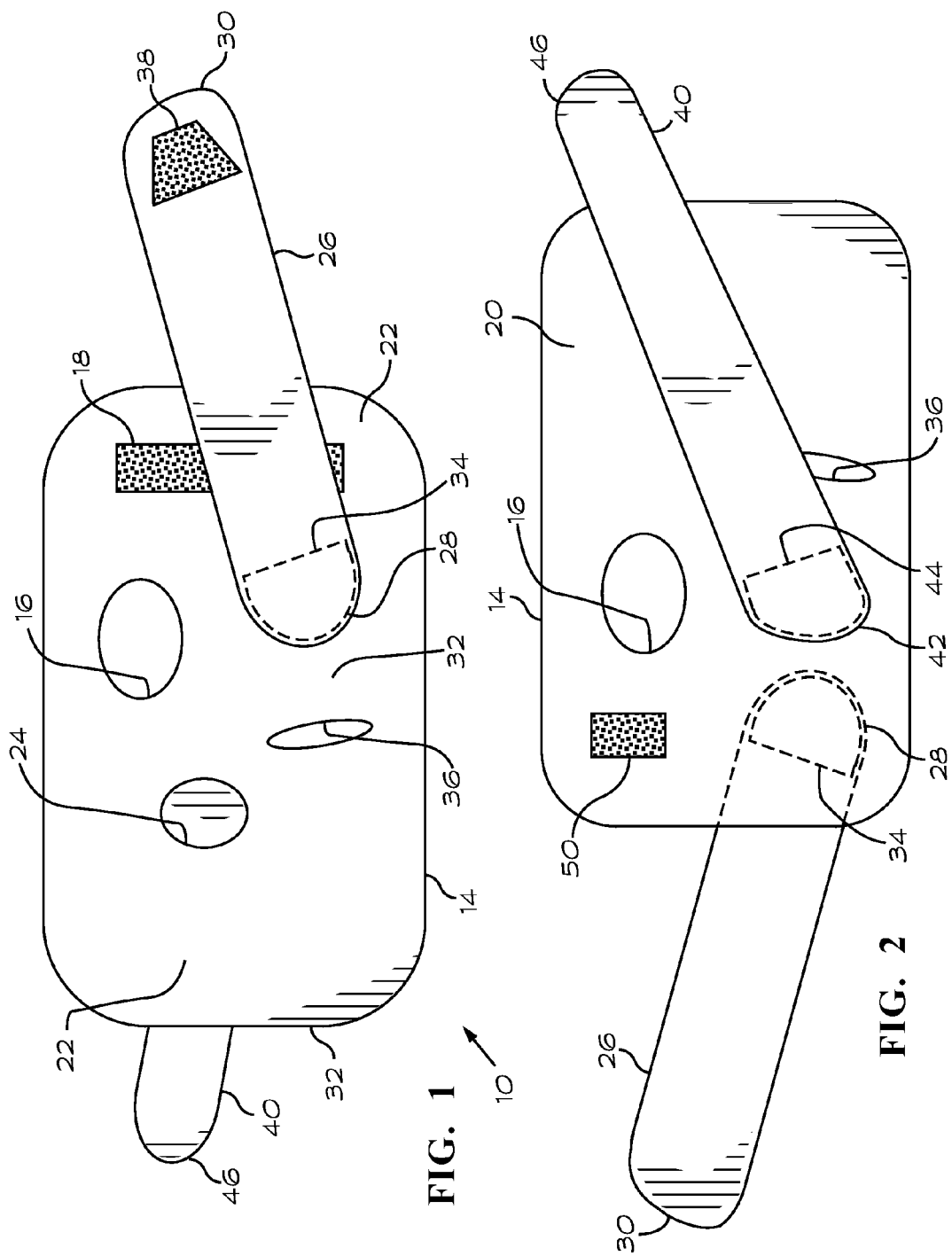

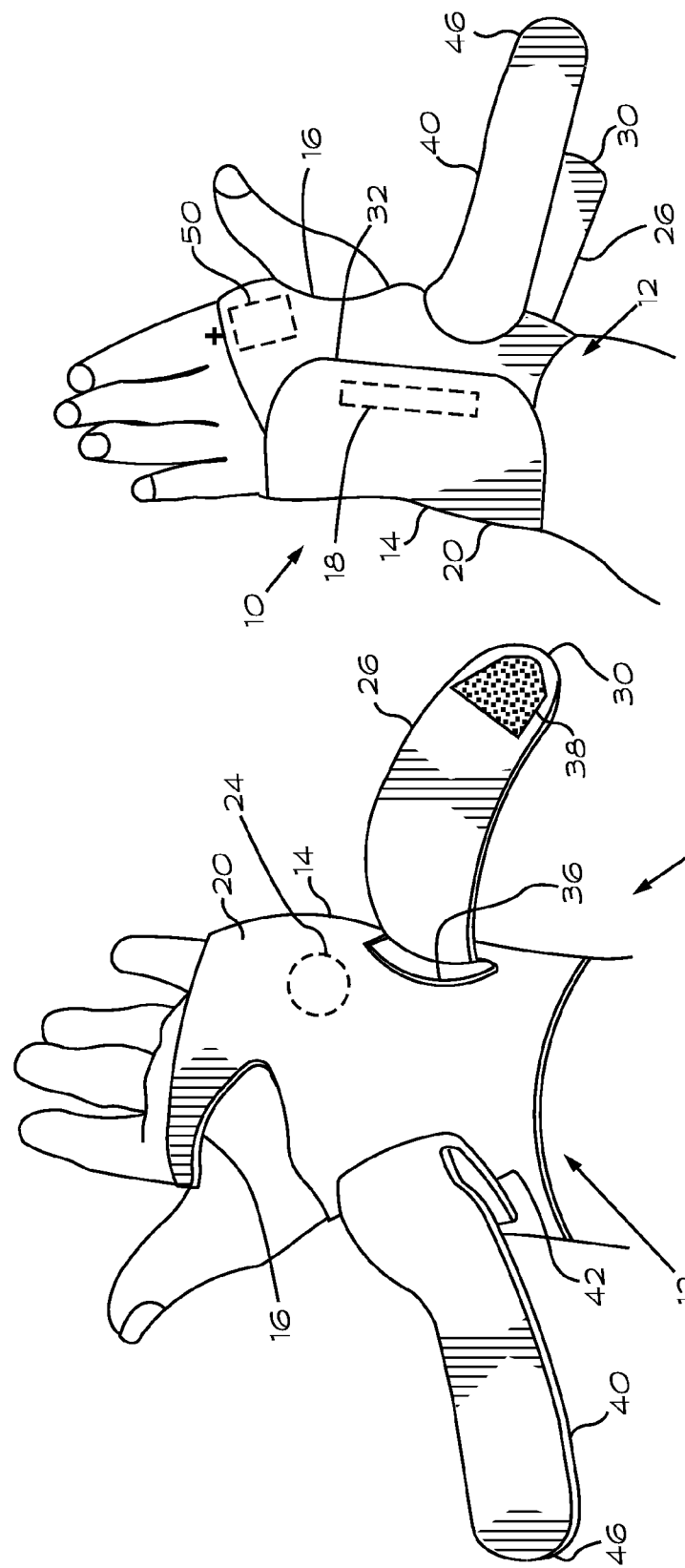

ULNAR SIDED WRIST SUPPORT BRACE

CROSS REFERENCE TO RELATED APPLICATION

Priority is claimed based on U.S. Provisional Application No. 61/796,308, filed Nov. 8, 2012.

BACKGROUND OF THE INVENTION

1. Field of the Invention

This invention relates generally to orthopedic devices and particularly to a wrist support brace for alleviating ulnar sided wrist pain in patients suffering from wrist injuries.

2. Description of the Prior Art

Ulnar sided wrist pain is a common problem in people with wrist injuries such as triangular fibrocartilage complex sprains/tears, ulnar impaction syndrome, wrist fractures, wrist sprains/strains and wrist tendonitis on the ulnar side. Prior art products do not provide support to both depression of the ulnar styloid and distal radial ulnar joint, while also lifting the area of the ulnar carpus. The prior art wrist braces address only lifting the carpus or supporting the distal radial ulnar joint. Nothing prior to the present invention is able to provide support in both directions at the same time, providing a counterforce to the ulnar side of the wrist.

SUMMARY OF THE INVENTION

An object of the invention is to provide an ulnar sided wrist brace suitable for physical and occupational therapy clinics, doctors and athletic trainers to provide to individuals suffering with ulnar sided wrist pain.

The present invention overcomes problems associated with prior art wrist support devices by boosting the ulnar carpus and compressing the ulnar styloid. The ulnar sided wrist brace according to the present invention provides support to the triangular fibrocartilage complex, supports the extensor carpi ulnaris tendon and decreases overall stress on the ulnar side of the wrist. It also supports ulnar carpal region to alleviate sagging. The present invention prevents ulnar carpal sagging by lifting the ulnar carpus dorsally and depressing the ulnar styloid volarly, thereby decreasing stress on the ulnar wrist anatomic structures. Prior art products either support the ulnar carpus or support the distal radial ulnar joint. No device other than the present invention does both at the same time.

A wrist brace for alleviating ulnar sided wrist pain comprises a base panel having an inner surface and an outer surface, the base panel having a thumbhole and a strap slit formed therein and a wrist strap having a first wrist strap end and a second wrist strap end, the wrist strap first end being connected to the inner surface of the base panel, the wrist strap being formed to wrap around a patient's wrist directly over the patient's ulnar styloid to provide volar compression, with the second wrist strap end extending through the strap slit for connection to the outer surface of the base panel, and an oblique strap having a first oblique strap end and a second oblique strap end, the first oblique strap end being connected to the outer surface of the base panel and arranged to wrap from the patient's volar radial wrist over the patient's ulnar carpus at an oblique angle on the base panel with the second oblique strap end attaching to the outer surface of the base panel dorsally near the distal to mid-shaft area of the patient's second metacarpal.

The base panel of wrist brace according to the present invention is preferably formed to comprise an elastic material.

The outer surface of the base panel of the wrist brace according to the present invention preferably is comprised of a loop material suitable for being attached to an adjacent hook material.

The wrist brace of according to the present invention preferably further comprises a detachable pad mounted to the inner surface of the base panel and located such that when a patient inserts a thumb through the thumbhole, the patient's pisiform is adjacent the detachable pad.

A method according to the present invention for preventing ulnar carpal sagging by lifting the ulnar carpus dorsally and depressing the ulnar styloid volarly, thereby decreasing stress on the ulnar wrist anatomic structures comprises the steps of providing a base panel having a thumbhole and a wrist strap slit therein providing a wrist strap having a first wrist strap end and a second wrist strap end, connecting the wrist strap first end to an inner surface portion of the base panel, wrapping the wrist strap around the patient's wrist directly over the patient's ulnar styloid to provide volar compression thereof, extending the second wrist strap end through the wrist strap slit for connection to an outer surface portion of the base panel, providing an oblique strap having a first oblique strap end and a second oblique strap end, connecting the first oblique strap end to the outer surface of the base panel, wrapping the oblique strap from the patient's volar radial wrist over the patient's ulnar carpus at an oblique angle on the base panel and connecting the second oblique strap end to the outer surface of the base panel dorsally near the distal to mid-shaft area of the patient's second metacarpal.

The features and advantages of the present invention may be further understood and appreciated by referring to the drawings, which are not to any scale, and to the Detailed Description of the Invention.

BRIEF DESCRIPTION OF THE DRAWINGS

FIG. 1 is a bottom plan view illustrating an ulnar sided wrist brace according to the present invention lying flat and showing the inside of a base panel designed to touch the skin of a person using the device and further showing a straps for securing the base panel to the patient's wrist;

FIG. 2 top plan view illustrating the ulnar sided wrist brace of FIG. 1 lying flat and showing the outside of the base panel and further showing outside portions of the straps;

FIG. 4 is a perspective view showing the ulnar sided wrist brace of FIGS. 1-3 with the patient's left palm facing upward and with the straps unfastened from the base panel;

FIG. 5 is a perspective view showing the ulnar sided wrist brace of FIG. 4 from the dorsal side with the straps unfastened from the base panel;

DETAILED DESCRIPTION OF THE INVENTION

Figure 3:
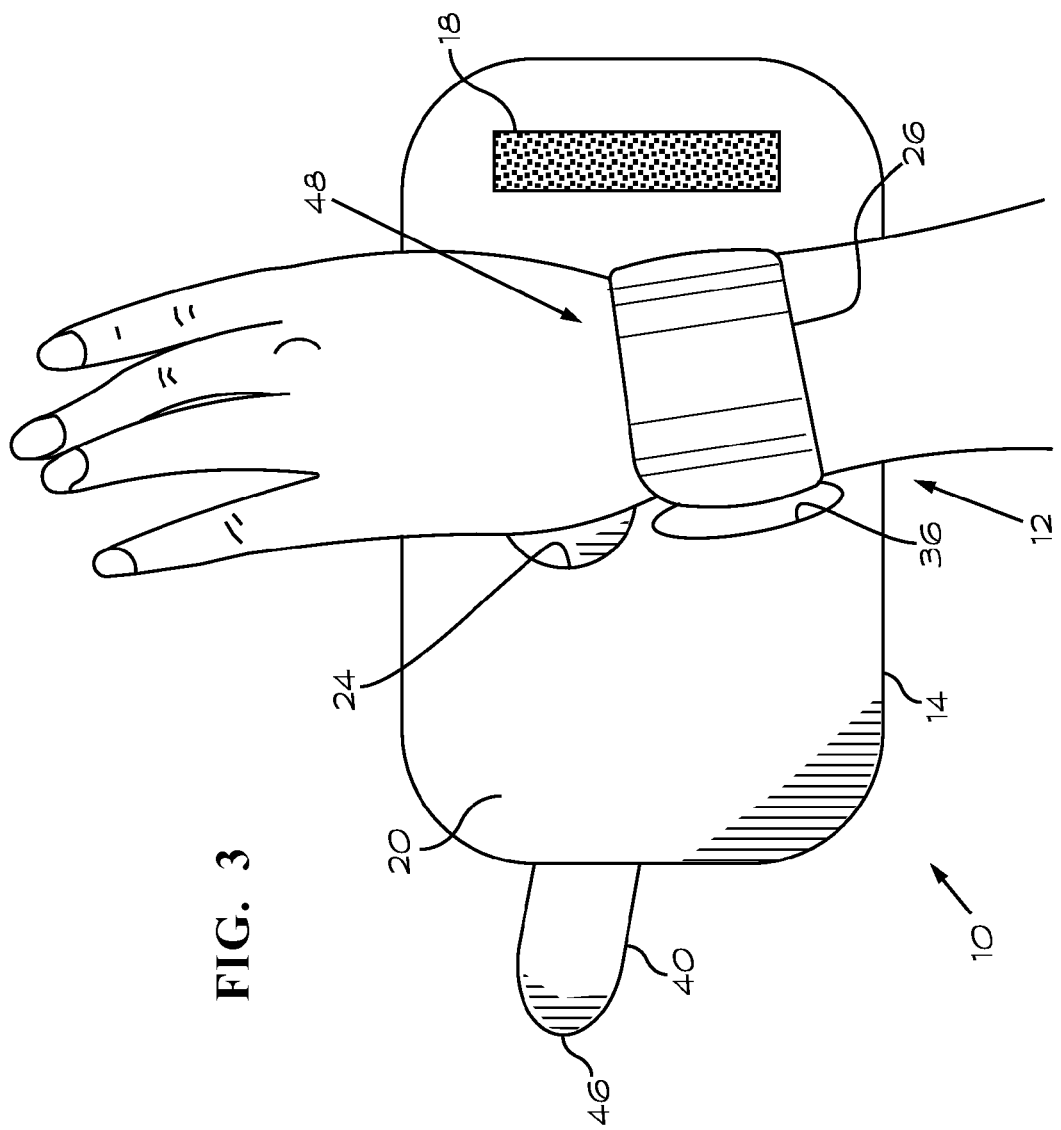
FIG. 3 is a bottom plan view showing the ulnar sided wrist brace according to the present invention with a patient's hand placed on the inside of the base panel with a first strap wrapped around the patient's wrist and threaded through a slit, and a second strap unfastened.

FIGS. 1-7 illustrate an ulnar sided wrist brace 10 according to the present invention. The ulnar sided wrist brace 10 supports the ulnar side of a patient's wrist 12 (FIGS. 3-7) to provide depression of the ulnar styloid dorsally while supporting the ulnar carpus and lifting the pisotriquetral joint volarly, thereby providing pain control and a counterforce support to the anatomical structures of the ulnar wrist. The styloid process of the ulna is at the distal end of a person's forearm, and it projects from the medial and dorsal part of the ulnar bone. It descends a little beyond the ulnar head and has a rounded end that affords attachment to the ulnar collateral ligament of the wrist as well as the radio-ulnar ligament.

The ulnar sided wrist brace 10 has a base panel 14 that is preferably formed of an elastic material. The base 14 has an outer surface 20 and an inner surface 22. The outer surface 20 is preferably comprised of a loop material so that hook fasteners can affix to it.

Figure 7:
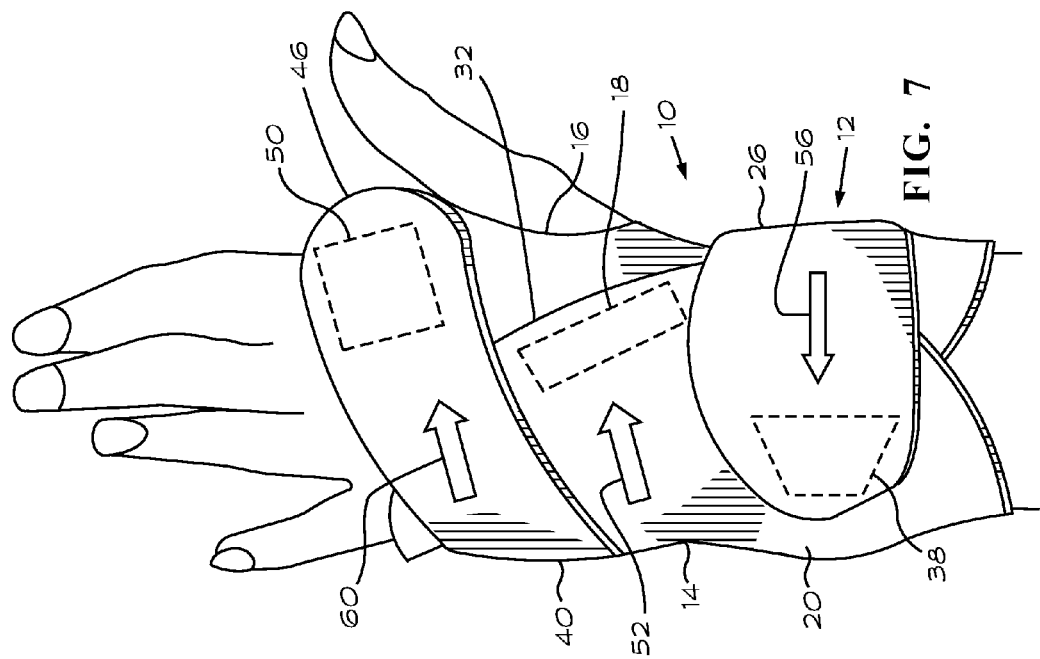
FIG. 7 is an illustration showing the dorsal side of the ulnar sided wrist brace of FIGS. 1-6 applied on the patient's left wrist with straps fastened to the base panel.

Referring to FIGS. 5 and 7, the base panel 14 wraps around the patient's wrist 12 and hand with the patient's thumb extending through a thumbhole 16. The base panel 14 and is fastened to the patient's hand by a hook fastener 18 adhering to the adjacent portion of the base panel 20. The hook fastener 50 is fastened to the base panel 20 in the area of the second metacarpal to provide an attachment for end 46 of strap 40.

As shown in FIGS. 1-3 and 6 a flexible wrist strap 26 having ends 28 and 30 wraps directly over the patient's wrist ulnar styloid at an inside region 32 of the base panel 14. The end 28 preferably is fastened to the base panel 14 by stitching 34. The end 30 of the flexible wrist strap 26 courses over the dorsal wrist 48, threads through a strap slit 36 in the base panel 14 and courses to the outer surface 20 of the base panel 14 to fasten to the base panel 14 by a hook fastener 38, depressing the ulnar styloid. A somewhat stiff oblique strap 40 has an end 42 that is preferably fastened to the base panel 14 by stitching 44. The oblique strap 40 has an and end 46 that is wrapped in an oblique fashion over the region of the patient's pisiform bone and is wrapped around to the dorsal side 48 of the wrist 12 to be fastened to a hook fastener 50 providing a counter force on the patient's ulnar styloid dorsally and ulnar carpus volarly, thereby unloading the ulnar wrist soft tissue structures. A pad 24 is affixed to the inner surface 22 of the base panel 14 to be adjacent the patient's pisiform bone to provide more volar support of the patient's ulnar carpus. The pad 24 is preferably removable and formed of a soft material such as foam. The position of the pad 24 is adjustable so that the pad 24 is adjacent the patient's pisiform bone.

Figure 6:
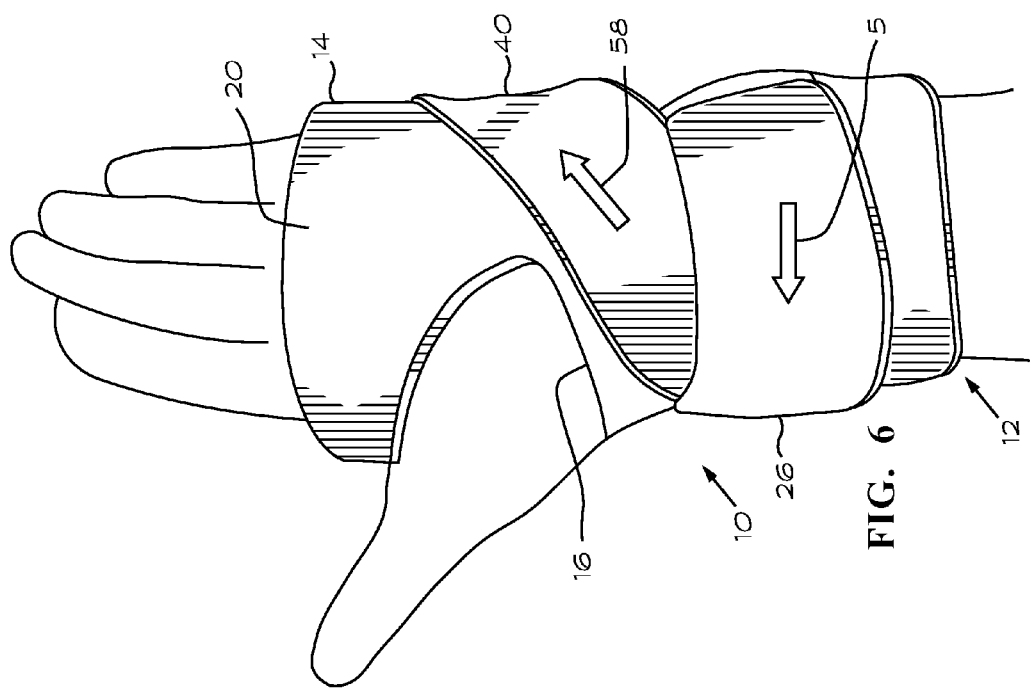
FIG. 6 is an illustration showing the volar side of the ulnar sided wrist brace according to the present invention applied on a patient's left wrist with straps wrapped around the base panel.

Proper placement of the ulnar sided wrist brace 10 on a patient involves positioning the patient's hand and wrist 12 on the inside surface 22 of base panel 14 as shown in FIG. 3. The wrist strap 26 is wrapped around the patient's wrist 12 and then the end 30 is passed through the strap slit 36. FIG. 4 shows the end 30 of the wrist strap 26 after it has passed through the strap slit 36. As shown in FIGS. 5-7, the base panel 14 is wrapped around the patient's hand and wrist as indicated by the arrow 52, and the hook fastener 18 is affixed to the outer surface 20 near the center of the dorsal side of the patient's hand. Referring to FIGS. 6 and 7, the wrist strap 26 is wrapped around the patient's wrist 12 as indicated by the arrows 54 and 56 and is fastened to the outer surface 20 by the hook fastener 38. The oblique strap 40 is wrapped around the patient's hand at an angle so that it passes below the thumb on the volar side as indicated by the arrows 58 and 60 and coursing over the pad 24. The oblique strap 40 then wraps around to the dorsal side of the hand and is fastened to the outer surface 20 by the hook fastener 50.

Ulnar wrist support is provided by the two straps 26 and 40, which wrap in opposite directions to provide compression over the patient's dorsal ulnar styloid in a volar direction and compression of the patient's pisotriquetral joint in a dorsal direction to provide better alignment of the ulnar wrist soft tissues and wrist joint. The ulnar sided wrist brace 10 according to the present invention will be made in right and left hand versions with the same anatomical principles, and will essentially be reversed on opposite hands.

The ulnar sided wrist brace 10 functions by wrapping the base panel 14 circumferentially around the patient's wrist 12 with the thumb through the thumbhole 16 to provide overall support to the patient's wrist 12. The wrist strap 26 then depresses the patient's ulnar styloid as it wraps radially around the patient's ulna and comes out of the strap slit 36 in the base panel 14 to be secured using the hook fastener 38. The oblique, stiff oblique strap 40 courses over the pad 24 to push the patient's ulnar carpus dorsally and affixes to the hook fastener 50. The counter force of ulnar styloid depression in a volar direction and ulnar carpus compression in a dorsal direction provides better anatomical alignment of the soft tissue structures on the ulnar side of the wrist and limits ulnar wrist sagging.

The unique features of this brace arise from the strapping. The oblique strap 40 wrapping from the volar radial wrist over the ulnar carpus and attaching at an oblique angle on the brace dorsally near the distal to mid-shaft area of the second metacarpal provides support not offered with any other brace for ulnar sided wrist pain. The flexible circumferential wrist strap 26 directly over the ulnar styloid providing depression in a volar direction in conjunction with the oblique strap provides a stabilizing effect on the ulnar wrist with counter forces that no other wrist brace can offer. In addition, having the two straps 26 and 40 wrap in opposite directions to provide this support is also a unique feature compared to all other braces.

Method for Manufacturing the Ulnar Sided Wrist Brace 10

The ulnar sided wrist brace 10 is preferably fabricated by cutting the thumbhole 16 and slit 36 in the stretchable base panel 14. The wrist strap 26 preferably is affixed to the inside of the brace via stitching 28 with needle and thread and wraps in a circumferential manner around the patient's wrist. The oblique strap 40 also is preferably affixed to the outside of the base panel 14 via stitching 44 with needle and thread and wraps obliquely around the ulnar side of the patient's wrist over the pad 24. The hook fasteners 18, 38 and 50 are also preferably secured with needle and thread. The pad 24 preferably is affixed to the base by way of a double-sided adhesive backing or by a hook and loop fastener so that the exact position of the pad 24 can be adjusted as needed. The pad 24 preferably is formed as a round disc cut out of a high-density foam material or silicone.

Alternative Embodiments of Invention

The base material can be any stretchy material like neoprene and can be modified with loop fasteners lining up with the described hook fasteners if the material does not provide for the ability to hook to the hook fastener naturally. The cut outs of the thumbhole 16 and the slit 36 for the wrist strap 26 may be reinforced with stitching to provide extra durability. The oblique strap 40 can be any suitably stiff material or reinforced stretchy material with limited stretch. The oblique strap 40 may also be connected to the base using a rivet or other mechanism that allows the strap to pivot. The soft pad 24 may be made out of high-density foam, silicone, or any other soft/dense material to increase support through the ulnar carpus. A rigid stay in the volar part of the brace could be added to provide a more rigid support to the wrist. The stay would be slid into a pouch that could be sewed in a strip on the base of the brace. In addition, another soft pad using foam, silicone, or neoprene can be placed on the wrist strap 26 to increase pressure over the ulnar styloid.

What is claimed is:

1. A wrist brace for alleviating a patient's ulnar sided wrist pain by applying targeted pressure to align the patient's carpal bones, comprising:
    a base panel formed of an elastic material and having an inner surface and an outer surface, the base panel having a thumbhole and a strap slit formed therein;
    a wrist strap for wrapping around a patient's wrist directly over the patient's ulnar styloid for providing volar compression and having a first wrist strap end and a second wrist strap end, the first wrist strap end being connected to the inner surface of the base panel, with the second wrist strap end extending through the strap slit for connection to the outer surface of the base panel;
    an oblique strap for wrapping in a direction opposite from the wrist strap from the patient's volar radial wrist over the patient's ulnar carpus at an oblique angle on the base panel and having a first oblique strap end and a second oblique strap end, the first oblique strap end being connected to the outer surface of the base panel with the second oblique strap end attaching to the outer surface of the base panel dorsally near the distal to mid-shaft area of the patient's second metacarpal, the wrist strap and the oblique strap cooperating to apply oppositely—directed compressive forces to the patient's ulnar styloid and pisiform bone; and
    a detachable pad mounted to the inner surface of the base panel, the detachable pad having an adjustable location such that when a patient inserts a thumb through the thumbhole, the patient's pisiform bone is adjacent the detachable pad, the detachable pad providing volar support of the patient's ulnar carpus.

2. The wrist brace of claim 1 wherein the outer surface of the base panel comprises a loop material suitable for being attached to an adjacent hook material.

3. A method for alleviating a patient's wrist pain caused by ulnar carpal sagging by lifting the ulnar carpus dorsally and depressing the ulnar styloid volarly, thereby decreasing stress on the ulnar wrist anatomic structures, comprising the steps of:
    providing a base panel formed of a flexible material and having a thumbhole and a wrist strap slit therein;
    providing a wrist strap having a first wrist strap end and a second wrist strap end;
    connecting the wrist strap first end to an inner surface portion of the base panel;
    mounting a detachable pad to the inner surface of the base panel in an adjustable location such that when a patient inserts a thumb through the thumbhole, the patient's pisiform bone is adjacent the detachable pad, the detachable pad providing volar support of the patient's ulnar carpus wrapping the wrist strap around the patient's wrist directly over the patient's ulnar styloid to provide volar compression thereof;
    extending the second wrist strap end through the wrist strap slit for connection to an outer surface portion of the base panel
    providing an oblique strap having a first oblique strap end and a second oblique strap end;
    connecting the first oblique strap end to the outer surface of the base panel;
    wrapping the oblique strap from the patient's volar radial wrist over the patient's ulnar carpus at an oblique angle on the base panel; and
    connecting the second oblique strap end to the outer surface of the base panel dorsally near the distal to mid-shaft area of the patient's second metacarpal.

\* \* \* \* \*